United States Patent [19]

Deeg et al.

[11] Patent Number: 4,868,139
[45] Date of Patent: Sep. 19, 1989

[54] AQUEOUS CHOLESTEROL STANDARD SOLUTION AND PROCESS FOR ITS PREPARATION

[75] Inventors: Rolf Deeg, Seeshaupt; Gisela Dengler, Wielenbach; Joachim Ziegenhorn, Starnberg, all of Fed. Rep. of Germany

[73] Assignee: Boehringer Mannheim GmbH, Mannheim, Fed. Rep. of Germany

[21] Appl. No.: 122,019

[22] Filed: Nov. 17, 1987

Related U.S. Application Data

[63] Continuation of Ser. No. 380,309, May 20, 1982, abandoned.

[30] Foreign Application Priority Data

Jun. 10, 1981 [DE] Fed. Rep. of Germany ....... 3122917

[51] Int. Cl.$^4$ ............................................. G01N 31/00
[52] U.S. Cl. ........................................... 436/13; 436/18
[58] Field of Search ........................ 435/11; 436/8–18; 252/408.1

[56] References Cited

U.S. PATENT DOCUMENTS

| | | | |
|---|---|---|---|
| 3,274,062 | 9/1966 | Lou | 167/84.5 |
| 3,733,279 | 5/1973 | Parekh et al. | 252/363.5 |
| 3,764,556 | 10/1973 | Kuchmak et al. | 252/408 |
| 3,859,047 | 1/1975 | Klein | 23/230 B |
| 3,876,375 | 4/1975 | Maurukas | 23/230 B |
| 3,891,573 | 6/1975 | Stary et al. | 252/408 |
| 4,042,330 | 8/1977 | Deshmukh | 23/230 B |
| 4,161,245 | 7/1979 | Berry | 435/11 |
| 4,164,448 | 8/1979 | Röeschlau et al. | 435/11 |
| 4,186,251 | 1/1980 | Tarbutton | 435/11 |
| 4,189,400 | 2/1980 | Proksch et al. | 252/408.1 |
| 4,226,713 | 10/1980 | Goldberg | 436/13 |

OTHER PUBLICATIONS

"Aqueous Primary Standard for use in Measuring Cholesterol by the Cholesteral Oxidase Method", Abele et al, *Clinical Chem*, vol. 25, No. 1, 1979, pp. 132–135.

"Disolution Rate Behavior of Solid Cholesterol Preparations in Bile Acid Solutions", Chem. Abstract No. 95: 103243x.

*Primary Examiner*—Barry S. Richman
*Assistant Examiner*—T. J. Wallen
*Attorney, Agent, or Firm*—Felfe & Lynch

[57] ABSTRACT

The present invention provides an aqueous cholesterol standard solution with a definite content of cholesterol, wherein it contains a detergent mixture of 10 to 90% of cholic acid and 90 to 10% of desoxycholic acid or of appropriate salts or derivatives of these acids.

The present invention also provides a process for the preparation of this aqueous cholesterol standard solution, wherein a detergent mixture of cholic acid and desoxycholic acid or of appropriate salts and derivatives of these acids is dissolved in distilled water or in 0.9% aqueous sodium chloride solution, an appropriate preservation agent and/or a buffer effective in the pH range of from 7 to 9 optionally added thereto, and a definite, precisely defined amount of cholesterol is dissolved in the solution thus obtained, while stirring and warming to 40° to 60° C.

26 Claims, No Drawings ial fluid. In general, this requirement can be
AQUEOUS CHOLESTEROL STANDARD SOLUTION AND PROCESS FOR ITS PREPARATION This is a continuation of application Ser. No. 380,309 filed on May 20, 1982, now abandoned.

This invention relates to a cholesterol standard. More specifically, the invention provides a cholesterol standard in the form of an aqueous solution of cholesterol which contains a defined amount of cholesterol and a detergent mixture.

BACKGROUND OF THE INVENTION

A series of chemical and enzymatic processes are known or have been suggested for the quantitative determination of cholesterol in various materials and especially in biological fluids. In the case of these processes, it is almost always necessary to introduce into the measurement cholesterol solutions with definite, known content of cholesterol as standard for the evaluation of the measurement results. For this purpose, use is made of cholesterol solutions with a defined cholesterol content, which are called cholesterol standards.

For the determination of cholesterol in biological fluids, as a rule standard solutions are necessary, the properties of which substantially coincide with those of the biological fluid. In general, this requirement can be fulfilled by the use of aqueous cholesterol standard solutions. In the case of a cholesterol standard solution, it is also important that it be sufficiently stable for comparatively long periods of time and that the cholesterol content remain absolutely constant. Hitherto, a series of aqueous cholesterol standard solutions have become known with a stable cholesterol content which remains constant for a comparatively long period of time. Thus, for example, Federal Republic of Germany patent specification No. 23 24 386 describes and claims an aqueous cholesterol standard solution which, in addition to a solubiliser, for example oxypolyethoxydodecane, and other component materials, contains from 1 to 20 volume percent of a primary or secondary aliphatic alcohol containing up to 4 carbon atoms. This cholesterol standard solution has proved to be stable and, even after storage for several years under normal conditions, shows an unchanged cholesterol content.

Federal Republic of Germany patent specification No. 28 39 433 describes an aqueous lipid standard solution which, in addition to a lipid, contains an ionic and a non-ionic detergent. With this composition there is said to be achieved, in particular, that, in the case of unavoidable standing of the sample, it evaporates as little as possible and the viscosity of the standard solution is not influenced.

Finally, from Clin. Chem., 25, 132–135/1979, there is known an aqueous cholesterol standard solution which, in addition to a definite and constant amount of cholesterol, contains sodium desoxycholate as solubiliser and which has proved to be useful for the enzymatic determination of cholesterol.

The previously known cholesterol standard solutions are admittedly more or less useful for enzymatic cholesterol determinations by the so-called end value methods but they are useless for a kinetic cholesterol determination, such as is described, for example, in Federal Republic of Germany patent specification No. 30 46 241.0. For this purpose, it is necessary to use a cholesterol standard which, in addition to the previously demanded requirements for such a standard with regard to stability and viscosity, must fulfill the additional requirement that its kinetic behaviour be identical to that of the sample to be determined. The previously known cholesterol standard solutions are useless for a kinetic cholesterol determination since their kinetic behaviour, because of their detergent content, differs considerably from that of the cholesterol samples to be measured.

BRIEF DESCRIPTION OF THE INVENTION

Therefore, it is an object of the present invention to provide an alcohol-free, stable, aqueous cholesterol standard solution, the kinetic behaviour of which is comparable, in the case of enzymatic cholesterol determinations, with that of the cholesterol samples to be measured.

Thus, according to the present invention, there is provided an aqueous cholesterol standard solution with a definite content of cholesterol, wherein it contains a detergent mixture of 10 to 90% of cholic acid and 90 to 10% of desoxycholic acid or of appropriate salts or derivatives of these acids.

A solution of cholesterol in the above-defined detergent mixture of cholic acid and desoxycholic acid or of appropriate salts or derivatives of these acids has proved to be stable for a comparatively long period of time and to be of sufficiently low viscosity, Furthermore, it has been shown that by combination of the two detergents, the kinetic behaviour of the cholesterol standard according to the present invention can, surprisingly, be optimally adapted to the kinetic behaviour of the cholesterol-containing sample.

DETAILED DESCRIPTION OF THE INVENTION

Within the scope of the cholesterol standard solution according to the present invention, a detergent mixture is preferred which contains the cholic acid and desoxycholic acid or appropriate salts or derivatives thereof in a ratio of 40:60 to 60:40. For a kinetic cholesterol determination according to Federal Republic of Germany patent specification No. 30 46 241.0, a cholesterol standard has proved to be especially advantageous which, as detergent mixture, contains equal portions of sodium cholate and sodium desoxycholate. The cholesterol standard solution according to the present invention may contain 10 to 300 g./liter and preferably 50 to 100 g./liter of the detergent mixture.

According to another preferred embodiment, the cholesterol standard solution according to the present invention additionally contains a buffer, the buffering range of which lies at a pH value of from 7 to 9. The buffer concentration is preferably within the range of from 10 to 100 mmol/liter. It has proved to be especially advantageous to use tris buffer with a pH of $8.0 \pm 0.2$ in a concentration of 50 mmol/liter.

In addition, for the prevention of bacterial attack, it has been proved to be advantageous to add thereto at least one appropriate preservation agent. All preservation agents can be used which do not influence the kinetic behaviour of the cholesterol standard, for example, sodium azide, germal or chloroacetamide. The preservation agents may be added to the standard solution in a concentration of from 0.1 to 10 mg./ml.

The cholic acid and desoxycholic acid are either used as such or preferably in the form of their salts, the sodium salts being especially preferred, or in the form of derivatives. As derivatives, there can be used, for example, glyco- or taurocholic acid or glyco- or taurodesoxycholic acid.

An especially preferred cholesterol standard according to the present invention is one which contains 50 to 400 mg./dl. cholesterol
50 g./liter sodium cholate
50 g./liter sodium desoxycholate
1.0 g./liter sodium azide
2.5 g./liter chloroacetamide and
50 mmol/liter tris buffer (pH 8.0±0.2). For the preparation of the cholesterol standard solution according to the present invention, the cholic acid and the desoxycholic acid or their appropriate salts of derivatives are first dissolved in distilled water or 0.9% aqueous sodium chloride solution, which can additionally contain a preservation agent and/or a buffer, and thereafter a definite amount of cholesterol (up to 400 mg./100 ml. of solution mixture) is introduced, while stirring and gentle warming, preferably to 40° to 60° C.

The dissolving of the cholesterol in the detergent-containing solution can also take place advantageously by ultrasonic treatment. Furthermore, the preparation process can be modified in such a manner that the detergents and the cholesterol are dissolved in an appropriate, readily volatile organic solvent, for example methanol, the solution obtained is evaporated and the residue then again taken up in distilled water or in 0.9% aqueous sodium chloride solution, which can contain a preservation agent and/or buffer.

The cholesterol standard solution according to the present invention can be used not only for kinetic cholesterol determinations but also, in the same manner, for conventional enzymatic end value methods. Furthermore, it can also be used for the determination of HDL cholesterol. For this purpose, the standard can advantageously be diluted. This is preferably carried out with distilled water or with the precipitation reagent employed for the preliminary treatment of the sample, for example one containing phosphotungstic acid/magnesium ions.

The following Examples are given for the purpose of illustrating the present invention:

EXAMPLE 1

50 g. Sodium cholate and 50 g. sodium desoxycholate are dissolved in 500 ml. of 0.9% aqueous sodium chloride solution. 0.5, 1.0, 1.5, 2.0 or 4.0 g. cholesterol are introduced into the so-obtained solution with stirring and warming in a waterbath of about 50° C. After cooling to ambient temperature, the solution is made up to 1 liter with 0.9% aqueous sodium chloride solution.

The so-produced cholesterol standard according to the present invention displays, in the case of the enzymatic determination of cholesterol with the help of cholesterol oxidase from Streptomyces and 3,4-dichlorophenol, the same kinetic properties as samples containing total cholesterol, for example contron sera, human sera and the like.

EXAMPLE 2

50 g. Sodium cholate and 50 g. sodium desoxycholate, as well as 1 g. sodium azide, 2.5 g. chloroacetamide and 50 mmol tris buffer (pH 8.0±0.2) are dissolved in 500 ml. distilled water. The solution obtained is filtered through a membrane filter (0.2 to 0.4 μm.) and thereafter warmed to about 50° C. 0.5 ,1.0, 1.5, 2.0 or 4.0 g. cholesterol are added thereto and the mixture stirred for 10 to 30 minutes. Thereafter, the solution is allowed to cool and is made up to 1 liter with distilled water.

It will be understood that the specification and examples are illustrative but not limitative of the present invention and that other embodiments within the spirit and scope of the invention will suggest themselves to those skilled in the art.

What is claimed is:

1. Aqueous cholesterol standard solution having a predetermined content of cholesterol and comprising a detergent mixture, said detergent mixture having by weight 10 to 90% of a compound selected from the group consisting of cholic acid, salts of cholic acid and derivatives of cholic acid and 90 to 10% of a compound selected from the group consisting of desoxycholic acid, salts of desoxycholic acid, and derivatives of desoxycholic acid.

2. Cholesterol standard solution as claimed in claim 1, wherein the detergent mixture consists by weight of 40 to 60% of a compound selected from the group consisting of cholic acid, salts of cholic acid and derivatives of cholic acid, and 60 to 40% of a compound selected from the group consisting of desoxycholic acid, salts of desoxycholic acid and derivatives of desoxycholic acid.

3. Cholesterol standard solution as claimed in claim 1, which comprise a mixture of equal portions by weight of sodium cholate and sodium desoxycholate.

4. Cholesterol standard solution as claimed in claim 1, comprising the detergent mixture in a concentration of 10 to 300 g./liter.

5. Cholesterol standard solution as claimed in claim 4, comprising the detergent mixture in a concentration of 50 to 100 g./liter.

6. Cholesterol standard solution as claimed in claim 1, which additionally comprising 0.1 to 10 g./liter of at least one preservation agent.

7. Cholesterol standard solution as claimed in claim 1, wherein cholic acid and desoxycholic acid constitute the detergent mixture.

8. Cholesterol standard solution as claimed in claim 1, which additionally comprises 10 to 100 mmol/liter of a buffer effective in the pH range of from 7 to 9.

9. Cholesterol standard solution as claimed in claim 1, which additionally comprises 0.1 to 10 g./liter of at least one preservation agent and 10 to 100 mmol/liter of a buffer effective in the pH range of from 7 to 9.

10. Cholesterol standard solution as claimed in claim 9, containing:
50 to 400 mg./dl. cholesterol
50 g./liter sodium cholate
50 g./liter sodium desoxycholate
1.0 g./liter sodium azide
2.5 g./liter choloacetamide and
50 mml./liter tris buffer (pH 8.0±0.2).

11. Process for the preparation of an aqueous cholesterol standard solution having a predetermined content of cholesterol and comprising a detergent mixture of by weight 10 to 90% of a compound selected from the group consisting of cholic acid, salts of cholic acid and derivatives of cholic acid and 90 to 10% of a compound selected from the group consisting of desoxycholic acid, salts of desoxycholate acid, and derivatives of desoxycholic acid, which process comprises dissolving said detergent mixture in distilled water, and dissolving a predetermined amount of cholesterol in the thus obtained solution while stirring and warming to 40° to 60° C.

12. Process as claimed in claim 11, wherein a buffer effective over pH 7 to 9 is added to the solution prior to the addition of cholesterol.

13. Process as claimed in claim 11, wherein a preservation agent is added to the solution prior to the addition of cholesterol.

14. A method for kinetically determining cholesterol in a biological fluid which comprises using, as a cholesterol standard, a solution having a predetermined content of cholesterol and a detergent mixture of from 10 to 90% by weight of a compound selected from the group consisting of cholic acid, salts of cholic acid and derivatives of cholic acid, and from 90 to 10% by weight of a compound selected from the group consisting of desoxycholic acid, salts of desoxycholic acid and derivatives of desoxycholic acid, determining the cholesterol in said biological fluid and in said standard, and comparing the cholesterol in said biological fluid against said standard.

15. A method according to claim 14 in which the detergent is a mixture of from 40 to 60% of a compound selected from the group consisting of cholic acid, salts of cholic acid and derivatives of cholic acid, and from 60 to 40% of a compound selected from the group consisting of desoxycholic acid, salts of desoxycholic acid and derivatives of desoxycholic acid.

16. A method according to claim 15 in which the detergent mixture consists of about equal portions by weight of sodium cholate and sodium desoxycholate.

17. A method according to claim 14 wherein, in the cholesterol standard, the detergent mixture is present in a concentration of from 10 to 300 g./liter.

18. A method according to claim 17 in which the detergent mixture is present in a concentration of from 50 to 100 g./liter.

19. A method according to claim 14 in which the standard solution additionally contains from 0.1 to 10 g./liter of at least one preservation agent.

20. A method according to claim 14 in which the detergent mixture consists essentially of cholic acid and desoxycholic acid.

21. A method according to claim 14 in which the standard solution additionally contains from 10 to 100 mmole/liter of a buffer effective in the pH range of from 7 to 9.

22. A method according to claim 14 in which the standard solution additionally contains from 0.1 to 10 g./liter of at least one preservation agent and from 10 to 100 mmole/liter of a buffer effective in the pH range of from 7 to 9.

23. A method according to claim 22 in which the standard solution comprises:
   50 to 400 mg./dl. cholesterol
   50 g./liter sodium cholate
   50 g./liter sodium desoxycholate
   1.0 g./liter sodium azide
   2.5 g./liter chloroacetamide and
   50 mmol/liter tris buffer (pH $8.0\pm0.2$).

24. Process for the preparation of an aqueous standard solution having a predetermined content of cholesterol and comprising a detergent mixture of by weight 10 to 90% of a compound selected from the group consisting of cholic acid, salts of cholic acid and derivatives of cholic acid and 90 to 10% of a compound selected from the group consisting of desoxycholic acid, salts of desoxycholic acid, and derivatives of desoxycholic acid, which process comprises dissolving said detergent mixture in 0.9% aqueous sodium chloride solution, and dissolving a predetermined amount of cholesterol in the thus obtained solution while stirring and warming to 40° to 60°.

25. Process as claimed in claim 24, wherein a buffer effective over pH 7 to 9 is added to the solution prior to the addition of cholesterol.

26. Process as claimed in claim 24, wherein a preservation agent is added to the solution prior to the addition of cholesterol.

* * * * *